United States Patent [19]

Clayson et al.

[11] Patent Number: 4,727,206
[45] Date of Patent: Feb. 23, 1988

[54] PRODUCTION OF AROMATICS FROM HYDROCARBON FEEDSTOCK

[75] Inventors: David M. Clayson, Walton-on-Thames; Timothy K. McNiff, Weybridge, both of England

[73] Assignee: British Petroleum Company p.l.c., London, England

[21] Appl. No.: 938,573

[22] Filed: Dec. 5, 1986

[30] Foreign Application Priority Data

Dec. 23, 1985 [GB] United Kingdom ............... 8531687

[51] Int. Cl.$^4$ .................................................. C07C 2/00
[52] U.S. Cl. .................................... 585/415; 585/417; 585/943
[58] Field of Search ..................... 585/415, 417, 943

[56] References Cited

U.S. PATENT DOCUMENTS

| | | | |
|---|---|---|---|
| 3,760,024 | 9/1973 | Cattanach | 585/415 |
| 3,775,561 | 11/1973 | Kaiding et al. | 585/417 |
| 3,855,115 | 12/1974 | Morrison . | |
| 4,056,575 | 1/1977 | Gregory et al. | 585/417 |
| 4,120,910 | 10/1978 | Chu . | |
| 4,350,835 | 9/1982 | Chester et al. | 585/417 |
| 4,490,569 | 12/1984 | Chu et al. | 585/415 |
| 4,497,970 | 2/1985 | Young | 585/417 |
| 4,613,716 | 9/1986 | McNiff | 585/417 |

FOREIGN PATENT DOCUMENTS 747847  7/1980  U.S.S.R. ................. 585/500

*Primary Examiner*—William R. Dixon, Jr.
*Assistant Examiner*—Cynthia A. Prezlock
*Attorney, Agent, or Firm*—Brooks Haidt Haffner & Delahunty

[57] ABSTRACT

This invention relates to the aromatization of methane rich hydrocarbon feedstock by contact with a gallium loaded zeolite containing a Group VIIB metal or metal compound as catalyst. The preferred metal is rhenium. The reaction proceeds at a temperature between 600°–800° C. in the absence of oxygen. The reaction products are useful as gasoline blending components.

9 Claims, No Drawings

PRODUCTION OF AROMATICS FROM HYDROCARBON FEEDSTOCK

The present invention relates to a process for producing liquids rich in aromatic hydrocarbons from a hydrocarbon feedstock containing a major proportion of methane.

Hitherto synthetic routes to producing aromatics from open chain hydrocarbons have started from feedstocks which have at least two carbon atoms. Such feedstocks are initially dimerised or oligomerised and the dimerised or oligomerised product is subsequently cyclised over a variety of catalysts at temperatures in the region of 500°–600° C. Such processes are described for example in our British Pat. Nos. 1507778 and 1561590. According to the British Pat. No. 1561590 a gallium catalyst supported on an aluminosilicate in which the ratio of silica to alumina is between 20:1 and 70:1 is used.

It has now been found that aromatics may be produced from hydrocarbon feedstocks containing less than two carbon atoms.

Accordingly, the present invention is a process for producing liquids rich in aromatic hydrocarbons comprising bringing into contact at a temperature between 600° C. and 800° C. a hydrocarbon feedstock containing a major proportion of methane with a catalyst composition comprising an aluminosilicate having silica to alumina in a molar ratio of at least 5:1, said aluminosilicate being loaded with (i) gallium or a compound thereof and (ii) a metal or a compound thereof from Group VIIB of the Periodic Table.

The term "Periodic Table" referred to herein refers to the table appearing at pages 448 and 449 of the Handbook of Chemistry and Physics, Ed. Hodgman, C. D. et al and published by The Chemical Rubber Publishing Company, Cleveland, Ohio, USA (44th Edition), 1963.

The hydrocarbon feedstock has at least 50% w/w, preferably at least 70% w/w of methane and may be admixed with $C_2$ hydrocarbons. The $C_2$ hydrocarbon in the feedstock, if any, may be ethane, ethylene or mixtures thereof. The feedstock may contain in addition other open chain hydrocarbons containing between 3 and 8 carbon atoms as coreactants. Specific examples of such additional coreactants are propane, propylene, n-butane, isobutane, n-butenes and isobutene.

The aluminosilicate in the catalyst composition may be suitably zeolites e.g. those having an MFI type structure (cf. "Chemical Nomenclature, and Formulation of Compositions, of Synthetic and Natural Zeolites," IUPAC yellow booklet, 1978, and zeolite structure types published by The Structure Commission of the International Zeolite Association entitled "Atlas of Zeolite Structure Types", by Meier, W. M. and Olsen, D. H. (1978), distributed by Polycrystal Book Service, Pittsburgh, Pa, USA). The zeolites suitably have a silica to alumina ratio from 20:1 to 200:1 and may be represented by the general formula $M_{2/n}O.Al_2O_3.ySiO_2.zH_2O$ wherein M is a cation which is a positively charged ion selected from a metal ion or an organic ion of valence n and a proton, y is an integer greater than 5 and z is from 0 to 40. The metal cation, M, is preferably an alkali metal or alkaline earth metal ion, preferably sodium or potassium ions. The organic cations may be represented by the formula $R^1R^2R^3R^4N^+$ or by an ion derived from the amine $R^1R^2R^3N$, the diamine $R^1R^2N(CH_2)_xNR^3R^4$ or pyrrolidine where $R^1R^2R^3$ and $R^4$ may be H, $CH_3$, $C_2H_5$, $C_3H_7$, $C_4H_9$ or $-CH_2CH_2OH$ and x equals 2, 3, 4, 5 or 6. A typical example of an MFI zeolite is ZSM-5 although other zeolites, for example ZSM-8, ZSM-11, ZSM-12 and ZSM-35 may also be used. These zeolites are extensively described in a number of publications including U.S. Pat. No. 3,970,544 (Mobil). These zeolites are usually produced from a silica source, an alumina source, an alkali metal hydroxide and a nitrogen containing base as template. The nitrogen-containing base may be organic such as an alkanolamine, for example, diethanolamine or, inorganic e.g. ammonia. Zeolites made in this manner are described in our published European Patent Application Nos. 0002899, 0002900 and 0030811. Zeolites derived by the process of No. EP-A-30811 are preferred.

The gallium or gallium compound in the catalyst composition may be gallium oxide or it may be present as gallium ions if the cations in the aluminosilicate have been exchanged for gallium ions. Methods of loading zeolites with a gallium compound are well known and is published for instance in our No. EP-A-24930. The gallium ion or compound loaded zeolite may be reduced to metallic gallium during subsequent reduction treatment, if any, prior to contact with the feedstock.

Similarly, a metal or a compound thereof from Group VIIB of the Periodic Table may be incorporated into the catalyst composition by impregnation or ion-exchange. Specifically, the preferred metal is rhenium which may be present in the catalyst composition as the oxide, as an ion or as the reduced metal. The metals, oxides or ions may be suitably provided from a solution e.g. aqueous solution, of the respective metal salt such as for instance rhenium trichloride or ammonium perrhenate which may be subsequently oxidised or reduced prior to contact with the feedstock. Alternatively the gallium loaded zeolite may be intimately mixed with a Group VIIB metal compound.

The aluminosilicate may be loaded with the compounds of gallium and the Group VIIB metal in either order or a mixture of the two compounds may be used for simultaneous loading of the aluminosilicate. It is preferable to load the aluminosilicate with the Group VIIB metal compound prior to the addition of the gallium compound.

Whichever method of catalyst preparation is used, the amount of gallium present in the catalyst compositions may vary for instance from 0.05 to 10% by weight of the total aluminosilicate in the catalyst composition. The gallium exchanged or impregnated zeolite thus obtained may be combined with a porous matrix, e.g. silica or alumina or other inorganic compositions to improve the mechanical strength of the catalyst.

The amount of Group VIIB metal present in the catalyst composition is suitably from 0.05 to 10%, preferably from 0.1 to 1.0% w/w of the total composition.

The catalyst composition may be activated prior to contact with the hydrocarbon feedstock. The activation may be carried out by heating the catalyst at a temperature from 400° C. to 650° C., preferably from 500° C. to 600° C. Activation may be carried out in an atmosphere of hydrogen, air, steam or a gas inert under the reaction conditions such as nitrogen but preferably in an atmosphere containing hydrogen. The activation may be carried out in the reactor itself prior to the reaction. The catalyst composition is suitably used in a fixed bed, a moving bed or a fluidised bed.

The hydrocarbon feedstock is thereafter contacted in the vapour phase with the catalyst composition at a temperature from 600° to 800° C. preferably from 650° to 775° C. in the absence of oxygen. The reaction is suitably carried out at a pressure of 1–10 bar, preferably from 3–7 bar absolute. The weight hourly space velocity (WHSV) is suitably from 0.1–10, preferably from 0.5–5.0. Any unreacted methane recovered from the reaction products may be recycled to the aromatisation reaction.

The reaction products are useful as gasoline blending components.

The invention is further illustrated with reference to the following Examples.

In the Examples the following notations have been used:

SELECTIVITY =

$$\frac{\text{YIELD (PRODUCT)}}{\text{CONVERSION OF METHANE FEED}} \times 100$$

*WHSV* - Weight Hourly Space Velocity

*CT* - Contact Time

EXAMPLE 1

A sample of an MFI type zeolite containing ammonium cations (zeolite prepared using ammonia as template according to the general process of our published No. EP-A-0030811) was contacted with an aqueous solution of ReCl$_3$. The mixture was dried under vacuum at 130° C.

The rhenium impregnated zeolite was then contacted with an aqueous solution of gallium nitrate and dried under vacuum at 130° C.

The gallium/rhenium impregnated zeolite was bound in an inert silica matrix by mixing with an equal weight of LUDOX AS 40 (Registered Trade Mark) colloidal silica to obtain a slurry which was dried at 100° C. to give a hard cake which was broken up and sieved to give coarse particles which passed through a standard 12 mesh sieve but were retained by a 30 mesh sieve. This gave a final catalyst composition containing 0.7% w/w Ga and 0.4% w/w Re. These compositions were determined by X-ray fluorescence spectroscopy.

6.2 ml of this catalyst composition was taken and then loaded into a vertical fixed bed reactor. The catalyst composition was contacted with nitrogen and the temperature of the reactor raised to 600° C. over 45 minutes.

The catalyst composition was then contacted with H$_2$ at 600° C. for 2 hours prior to testing for methane aromatisation by contacting with methane at 700° C., 1 WHSV and 7 bar absolute pressure (CT-9.0 secs).

Analysis of the reaction products was carried out using an on-line, dual column gas chromatograph (POROPAK QS and OV101 silicone gum rubber columns) and the following results were obtained.

| CONVERSION OF METHANE Wt % | SELECTIVITY TO AROMATICS Wt % | AROMATICS YIELD Wt % |
| --- | --- | --- |
| 4.9 | 51.6 | 2.53 |

EXAMPLE 2

The catalyst composition was prepared and activated as in Example 1 above and tested for aromatisation of methane at 675° C., 1 WHSV and 7 bar absolute pressure (CT-9.25 secs) as in Example 1 above.

| CONVERSION OF METHANE Wt % | SELECTIVITY TO AROMATICS Wt % | AROMATICS YIELD Wt % |
| --- | --- | --- |
| 3.6 | 54.7 | 2.0 |

EXAMPLE 3

The catalyst composition was prepared and activated as in Example 1 above and tested for the aromatisation of methane at 750° C., 1 WHSV and 7 bar absolute pressure (CT 8.6 secs) as described in that Example.

| CONVERSION OF METHANE Wt % | SELECTIVITY TO AROMATICS Wt % | AROMATICS YIELD Wt % |
| --- | --- | --- |
| 8.3 | 35.4 | 2.95 |

We claim:

1. A process for producing liquids rich in aromatic hydrocarbons comprising bringing into contact at a temperature between 600° C. and 800° C. a hydrocarbon feedstock containing a major proportion of methane with a catalyst composition comprising an aluminosilicate having silica to alumina in a molar ratio of at least 5:1, said aluminosilicate being loaded with (i) gallium or a compound thereof and (ii) a metal or a compound thereof from Group VIIB of the Periodic Table; and wherein the hydrocarbon feedstock is brought into contact with the catalyst composition in the absence of oxygen.

2. A process according to claim 1 wherein the hydrocarbon feedstock has at least 70% w/w of methane.

3. A process according to claim 1 or 2 wherein the methane in hydrocarbon feedstock is mixed with C$_2$ hydrocarbons.

4. A process according to claim 1 or 2 wherein the aluminosilicate having a silica to alumina molar ratio of at least 5:1 is a zeolite selected from ZSM-5, ZSM-8, ZSM-11, ZSM-12 and ZSM-35.

5. A process according to claim 1 or 2 wherein the amount of gallium or a compound thereof in the catalyst composition is from 0.05 to 10% w/w of the total aluminosilicate in the composition.

6. A process according to claim 1 or 2 wherein the Group VIIB metal present as such or as a compound thereof in the catalyst composition is rhenium.

7. A process according to claim 1 or 2 wherein the amount of Group VIIB metal or a compound thereof present in the catalyst composition is from 0.05 to 10% w/w of the total catalyst composition.

8. A process according to claim 1 or 2 wherein the catalyst composition is heated at a temperature from 400°–650° C. prior to contact with the feedstock in an atmosphere selected from hydrogen, air, steam, or a gas inert under the reaction conditions.

9. A process according to claim 1, wherein the temperature is from 650° C. to 775° C.

* * * * *